(12) United States Patent
Rigler

(10) Patent No.: US 11,519,030 B2
(45) Date of Patent: Dec. 6, 2022

(54) SINGLE MOLECULE ANALYSIS IN AN ELECTRICAL FIELD

(71) Applicant: GNOTHIS HOLDING SA, Zug (CH)

(72) Inventor: Rudolf Rigler, Djursholm (SE)

(73) Assignee: Gnothis Holding AG, Zug (CH)

( * ) Notice: Subject to any disclaimer, the term of this patent is extended or adjusted under 35 U.S.C. 154(b) by 0 days.

(21) Appl. No.: 15/740,903

(22) PCT Filed: Jun. 28, 2016

(86) PCT No.: PCT/EP2016/065019
§ 371 (c)(1),
(2) Date: Dec. 29, 2017

(87) PCT Pub. No.: WO2017/001407
PCT Pub. Date: Jan. 5, 2017

(65) Prior Publication Data
US 2018/0187258 A1    Jul. 5, 2018

(30) Foreign Application Priority Data

Jun. 30, 2015  (EP) .................................. 15174524

(51) Int. Cl.
| | | |
|---|---|---|
| *C12Q 1/6874* | (2018.01) | |
| *G01N 1/40* | (2006.01) | |
| *G01N 21/64* | (2006.01) | |
| *B01L 3/00* | (2006.01) | |
| *G01N 15/10* | (2006.01) | |

(52) U.S. Cl.
CPC .......... *C12Q 1/6874* (2013.01); *B01L 3/5085* (2013.01); *G01N 1/40* (2013.01); *G01N 21/648* (2013.01); *G01N 21/6428* (2013.01); *B01L 2300/0645* (2013.01); *B01L 2300/0819* (2013.01); *G01N 21/6408* (2013.01); *G01N 2001/4038* (2013.01); *G01N 2015/1006* (2013.01); *G01N 2015/1081* (2013.01); *G01N 2021/6439* (2013.01)

(58) Field of Classification Search
CPC ..... B01L 2300/0645; B01L 2300/0819; G01N 21/6428; G01N 21/648; C12Q 1/6874
See application file for complete search history.

(56) References Cited

U.S. PATENT DOCUMENTS

| | | | |
|---|---|---|---|
| 6,582,903 B1 | 6/2003 | Rigler et al. | |
| 8,968,678 B2 | 3/2015 | Hu | |
| 2003/0059929 A1* | 3/2003 | Heller | B01J 19/0046 |
| | | | 435/287.2 |
| 2007/0020626 A1 | 1/2007 | Rigler | |
| 2010/0173792 A1 | 7/2010 | Heller et al. | |
| 2010/0261158 A1* | 10/2010 | Nordman | C12Q 1/6869 |
| | | | 435/6.1 |
| 2016/0326581 A1* | 11/2016 | Rigler | C12Q 1/6874 |

FOREIGN PATENT DOCUMENTS

| | | | |
|---|---|---|---|
| JP | H 09-503307 A | 3/1997 | |
| JP | H 11-502608 A | 3/1999 | |
| JP | 2014-112099 A | 6/2014 | |

OTHER PUBLICATIONS

Notification of Transmittal of the International Preliminary Report on Patentability cited in PCT/EP2016/065019 dated Sep. 27, 2017, 14 pages.
Written Opinion of the International Searching Authority and the International Search Report cited in PCT/EP2016/065019, dated Sep. 20, 2016, 2 pages.

* cited by examiner

*Primary Examiner* — Young J Kim
(74) *Attorney, Agent, or Firm* — Rothwell, Figg, Ernst & Manbeck, P.C.

(57) ABSTRACT

The invention relates to a process and a device for analysing single molecules, particularly to the parallel analysis of a plurality of single molecules. It is suitable for detecting interactions, e.g. binding between single molecules and/or reactions, e.g. elongation or degradation of single molecules. Particularly, the process of the invention relates to the sequencing of single nucleic acid molecules. The single molecule to be analysed is present in free form, i.e. dissolved or suspended in a liquid medium, within a reaction space formed around the sample spot. According to the present invention, an electrical field is applied across the reaction space, whereby a concentration of single molecules, at the sample spots is effected.

19 Claims, 1 Drawing Sheet

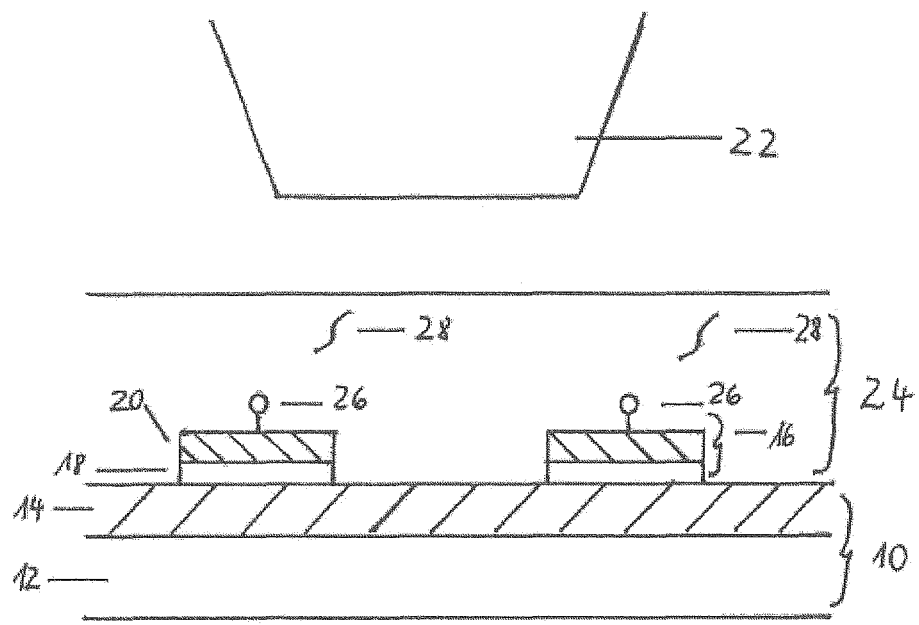
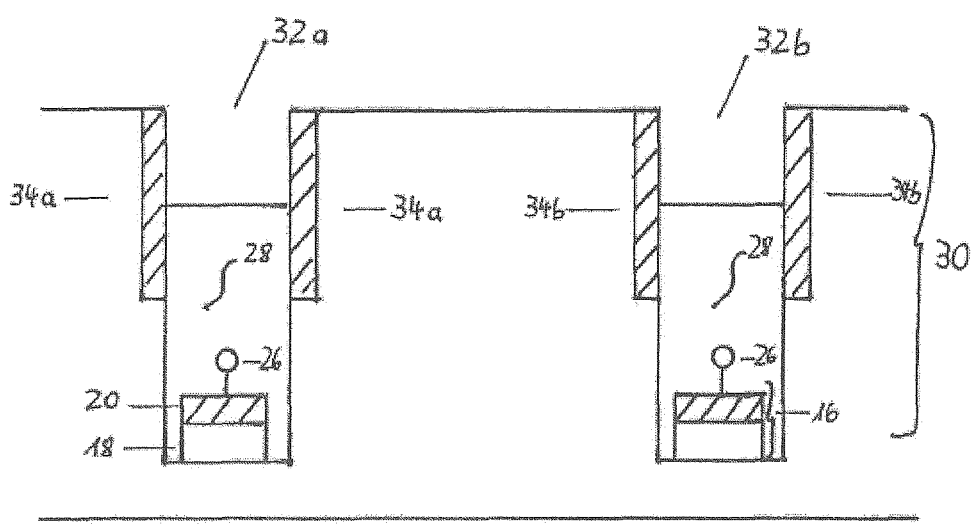

SINGLE MOLECULE ANALYSIS IN AN ELECTRICAL FIELD

CROSS REFERENCE TO RELATED APPLICATION

This application is a 35 U.S.C. 371 National Phase Entry Application from PCT/EP2016/065019, filed Jun. 28, 2016, which claims the benefit of European Patent Application No. 15174524.7 filed on Jun. 30, 2015, the disclosure of which is incorporated herein in its entirety by reference.

The invention relates to a process for analysing single molecules, in particular for sequencing of single nucleic acid molecules.

Sequencing of the human genome which consists of approx. $3 \times 10^9$ bases, or of the genome of other organisms and the determination and comparison of individual sequence variants requires the provision of sequencing methods which firstly are fast and secondly can be employed routinely and cost-effectively. Large efforts have been made in order to accelerate familiar sequencing methods, for example the enzymatic chain termination method according to Sanger et al. (Proc. Natl. Acad. Sci. USA 74 (1977) 5463), in particular by automation (Adams et al., Automated DNA Sequencing and Analysis (1994), New York, Academic Press).

The high demand for cost-efficient sequencing has driven the development of high-throughput sequencing technologies that parallelize the sequencing process producing a plurality of sequences concurrently. Examples of these sequencing technologies are massively parallel signature sequencing (Lynx Therapeutics), polony sequencing (Life Technologies), 454 pyrosequencing (Roche Diagnostics), illumina sequencing (Solexa Inc.), sequencing by ligation (Life Technologies), ion torrent semiconductor sequencing (Life Technologies) or DNA nanoball sequencing (Complete Genomics). These technologies allow rapid analysis of a consensus sequence in a nucleic acid population. Mutations existing in minority sequences in the nucleic acid population to be analysed, e.g. in a minority of cellular genomes, however, will not be detected since they are obscured by the majority of other sequences present in the population.

Another approach is single-molecule sequencing (Dörre et al., Bioimaging 5 (1997), 139-152), in which the sequence of nucleic acids is carried out by progressive enzymic degradation of fluorescently labelled single-stranded DNA molecules and by detection of the sequentially released monomeric molecules in a microstructure channel. This process has the advantage of only a single molecule of the target nucleic acid being sufficient for carrying out a sequence determination.

PCT/EP01/07462 discloses a multiplex sequencing process which comprises providing, in an immobilized form, nucleic acid molecules carrying a plurality of fluorescent labelling groups on a support and determining simultaneously the base sequence of a plurality of nucleic acid molecules on the basis of the time-dependent change, caused when nucleotide building blocks are cleaved off, in the fluorescence of said nucleic acid molecules or/and said cleaved-off nucleotide building blocks. According to WO 2003/052137, the sequence is determined by irradiating light into the support and generating an evanescent excitation field by way of internal reflection on the support surface in the region of the immobilized nucleic acid molecules.

WO 2006/013110 describes a multiplex sequencing process which comprises providing, in an immobilized form, nucleic acid-degrading and/or nucleic acid-synthesizing enzyme molecules, contacting the immobilized enzymes with free nucleic acid molecules and determining simultaneously the base sequence of a plurality of nucleic acid molecules on the basis of the time-dependent fluorescence change caused when nucleic acid building blocks are incorporated into and/or cleaved off from the nucleic acid molecules.

WO 2013/131888 discloses a process for parallel high-throughput sequencing of nucleic acid molecules, particularly in the single molecule, which involves the use of a circular nucleic acid template molecule.

Reference is also made to the paper "Brownian Motion of Single Molecule in Electric Field Electrophoresis" 2001, 22, 3813-3818.

Recently, single molecule sequencing technologies for determining the sequence of a single DNA strand have been developed, e.g. heliscope single molecule sequencing (Helicos Biosciences) or single molecule real time sequencing (Pacific Bioscience).

The approach of present commercial single-molecule DNA sequencing technologies to do DNA sequencing is that of so called consensus determination of a DNA sequence through the repeated analysis of several reads of identical DNA molecules. Hence, an accurate (preferably 99.9% or better) determination of the sequence of a DNA fragment is achieved by the analysis of several similar DNA fragments that are analysed and by the use of complex statistical algorithms to estimate the correct DNA sequence. The algorithms used by other single-molecule DNA sequencing technologies assume a priori that there exists only one sequence. Hence if there are minority parts of the sample that have differences in its sequence as compared with the other DNA molecules in the sample such differences in sequence will not be considered but will be treated by the algorithm as "noise" or "error". If the sample contains a mixture of DNA sequences at approximately the same concentrations the analysis will not be able to conclude a "consensus" sequence and the result will be void (invalid). The purpose of the complex algorithm is to, in as much as possible, compensate for other single-molecule DNA sequencing technologies' low primary accuracy of approximately 85-90%.

In order to overcome these problems, EP 14 150 807.7 discloses a process and a device for analysing single molecules, particularly for analysing a plurality of single molecules, more particularly for sequencing single nucleic acid molecules comprising the following features:

a support having at least one sample spot for positioning a single molecule to be analysed on a support, a light source, particularly a multipoint laser providing at least one illuminated volume element, e.g. a confocal volume element, at the position of the at least one single molecule on the support, and a detector, particularly a multipixel detector, which allows single photon detection from an individual single molecule on the support.

The problem underlying the present invention was to provide a support and a device for analysing single molecules, particularly for analysing a plurality of single molecules, more particularly for sequencing single nucleic acid molecules which allows an effective concentration of the single molecules to be analysed on the sample spot on the support. The inventor has found that by applying an electrical field across the reaction space of the single molecule detection, the molecules to be analysed, e.g. individual single nucleic acid molecules, can be concentrated by a factor of $10^2$ or more, $10^3$ or more or $10^4$ or more at the sample spots.

The present invention relates to a process for analysing a single molecule comprising the following steps:
 (a) providing a support comprising at least one individual sample spot thereon, wherein said sample spot is at least partially made from an electrically conductive material,
 (b) contacting said support with a liquid medium comprising at least one single molecule to be analysed, whereby a reaction space of liquid medium on said sample spot is formed,
 (c) applying an electrical field across said reaction space, whereby a concentration of said at least one single molecule to be analysed at said sample spot is effected, and
 (d) individually analysing said at least one single molecule.

The present invention particularly relates to a process for analysing a plurality of single molecules, comprising the following steps:
 (a) providing a support comprising a plurality of individual sample spots thereon, wherein said sample spots are at least partially made from an electrically conductive material,
 (b) contacting said support with a liquid medium comprising a plurality of single molecules to be analysed, whereby at least one reaction space on said sample spots is formed,
 (c) applying an electrical field across said reaction space, whereby a concentration of said single molecules at said sample spot is effected, and
 (d) individually analysing said single molecules.

The process of the invention relates to the analysis of a single molecule, particularly to the parallel analysis of a plurality of single molecules. It is suitable for detecting interactions, e.g. binding between single molecules and/or reactions, e.g. elongation or degradation of single molecules. Particularly, the process of the invention relates to the sequencing of single nucleic acid molecules.

In the present invention, a support is provided comprising at least one sample spot and particularly a plurality of individual sample spots for positioning single molecules to be analysed thereon. The spots may have a diameter in the range of about 1-20 nm, e.g. about 1-15 nm, about 2-15 nm or about 4-12 nm. In order to avoid crosstalk between individual spots, the distance between the centres of individual sample spots on the support (i.e. the sample spot distance) is preferably at least about 2 times the size of the spot diameter, more preferably at least about 3 times, at least about 5 times, at least about 10 times. The upper limit may be up to about 5000 nm, such as up to about 1000 nm, up to about 500 nm, up to about 100, or up to about 50 times the size of the spot diameter. The distance between the centres of individual sample spots on the support may have a distance range which is selected from any value of the lower and upper limits, e.g. from about 2 up to about 5000 times, or about 2 up to about 500 times, e.g. about 2 up to about 100 times about 5 to 500 times the size of the spot diameter.

The single molecule to be analysed is present in free form, i.e. dissolved or suspended in a liquid medium, within a reaction space formed around the sample spot. According to the present invention, an electrical field is applied across the reaction space, whereby a concentration of single molecules, particularly single nucleic acid molecules at (i.e. around or in the area of) the sample spots is effected. Thereby, the amount of single molecules to be analysed at the sample spot is substantially increased. For this purpose, the sample spot is at least partially made from an electrically conductive material. For example, the sample spot may have an electrically conductive surface. The surface of the sample spot may be a metal such as Au, Ag, Cr, Ni or Al, particularly a noble metal such as Au. In an especially preferred embodiment, the sample spot may comprise a plurality of different layers, e.g. metal layers, for example a first Cr layer and a second (top) Au layer.

The support may be any planar or structured support. Preferably, the support is planar. Examples of suitable support materials are glass, quartz, plastic, metals, semimetals such as silicon, for example, metal oxides such as silicon dioxide, for example, or composites comprising said materials. The support may, at least in the region of the sample spots, have sufficient optical transparency and suitable surface properties for irradiation with fluorescence excitation light or/and backscatter of fluorescence emission light through the support or for evanescence-based fluorescence detection.

In some embodiments, the support may comprise an electrically conductive material, e.g. a metal, metal oxide and/or polymer. For example, the support may have an at least partially electrically conductive surface in the area between individual sample spots. For example, the support may comprise a conductive surface layer with a thickness of e.g. 10-1000 nm, 20-500 nm or 50-200 nm, e.g. about 100 nm. The surface layer may be suitable metal oxide such as indium tin oxide or electrically conductive polymer.

In an especially preferred embodiment, the support is made from glass or quartz and has a conductive optically transparent surface. In an especially preferred embodiment, the support is from glass, e.g. ultra-pure quartz, having a thickness of e.g. about 0.175 nm and an electrically conductive transparent surface of e.g. about 100 nm thickness from a metal oxide such as indium tin oxide and/or an electrically conductive organic polymer.

The process of the present invention may be carried out in a single reaction space which is formed across the support or a portion thereof, on which the sample spots are located. Alternatively, the process may also be carried out in a multiplicity of separate reaction spaces across the support, wherein the separate reaction spaces are not in communication with each other, at least during certain steps of the process. Multiple separate reaction spaces may e.g. be formed by nano- and/or microwells and/or nano- or microspots on the support.

The process of the invention involves applying an electrical field across the reaction space. The individual electrically conductive sample spots, e.g. Au spots, may have the same electrical potential if an electrically conductive support surface is present between the individual spots. The electrical field may be applied between the electrically conductive sample spots and a further electrode, e.g. an electrically conductive structure of the optical measuring device, e.g. a metal case of the measuring objective. Alternatively, the counter electrodes may be represented by electrically conductive nano- or microwell wells if a structured support is used. Electrically conductive nano- or microwells may be generated by deposing a layer of an electrically conductive material, e.g. as described above, on the inner walls of nano- or mixrowells.

The applied electrical field may have a field strength from about 1-5000 V/cm, particularly about 10-2000 V/cm and more particularly about 20-200 V/cm. The electrical field is preferably applied with a direct current voltage, whereby charged molecules may migrate through the field into the direction of the electrode having an opposite charge. In a preferred embodiment, the electrical field has a strength of about 100 V/cm which may be achieved e.g. by applying an electrical field of 10 V between the tip of the optical measuring objective and the support plane at a distance of 1 mm. The field strength is chosen in order to provide a concentration of charged single molecules, e.g. negatively charged nucleic acid molecules at the support surface and in particular around the sample spots at which the optical analysis of the single molecules takes place. Alternatively, a support comprising a plurality of micro- or nanowells with sample spots therein and counter electrodes in the microwell walls may be used.

According to the present invention, at least one single molecule present on a sample spot is individually analysed. This optical analysis may comprise the following steps:

individually illuminating single molecules at individual sample spots with a light source, wherein the light source provides a plurality of individual illuminated volume elements at the sample spots, individually detecting light emitted from said single molecules with a light detector, wherein the light detector comprises a plurality of detection pixels, wherein said detection pixels on the detector preferably have a diameter in the range of about 0.5 µm-50 µm and the distance between said detection pixels is preferably at least about 2 times, more preferably about 3-10 times the diameter of the detection pixel, and correlating the detected light from an individual detection pixel with an event associated with a single molecule positioned on an individual spot.

Preferably an optical projection of a detection pixel on the support has a diameter in the range of about 100 nm-5 µm and wherein an individual sample spot is aligned to the projection of a single detection pixel on the support, particularly to the center of the projection of a single detection pixel on the support.

For illuminating single molecules at individual sample spots on the support, a light source suitable for multipoint-illumination, e.g. a laser light source may be used. Preferably, the light source is a multipoint light source, e.g. a multipoint laser light source. The light source is capable of providing a plurality of individual illuminated volume elements at the individual sample spots. The volume elements have a size from $10^{-10}$ to $10^{-24}$ l, e.g. from $10^{-12}$ to $10^{-21}$ l. Preferably, the volume elements may be confocal volume elements or evanescent fields generated by Total Internal Reflection (TIR). Preferably, the volume elements are evanescent fields generated by Total Internal Reflection (TIR). In a further embodiment the matrix of sample spots may be illuminated by a single beam from a light source, e.g. a laser light source.

The process of the invention comprises detection of light emitted from single molecules positioned on the support. Preferably, the detected light is emitted from optically detectable labelling groups, particularly from fluorescence labelling groups. The emitted light is subsequently detected with a light detector and correlated with an event associated with a single molecule positioned at an individual spot on the support.

Detection of emitted light may involve detection of lifetime of an excited state, and/or detection of rotational mobility and/or detection of lateral mobility and/or detection of a specific wavelength. Furthermore, it is possible to use Raman, Raman/Antistokes and/or surface-enhanced Raman (SER) based detection methods to identify single molecules.

Preferably, the detection of emitted light involves a lifetime detection optionally combined with the detection of a specific wavelength. For example, it has been shown that different components can be discriminated with an accuracy of 0.998 if their mean life times differ by around one nanosecond.

The event to be detected may be caused by e.g., association and/or dissociation of the labelling group with the single molecule to be analysed or by any other event causing a time-dependent change of light emission, e.g. a time-dependent fluorescence change.

Illuminating the volume element, e.g. the confocal volume element excites labelling groups present in the volume so that they emit light, e.g. fluorescent light, which is measured by means of the detector. The pattern of illuminated volume elements may be generated by a matrix of laser dots generated via diffractive optical elements, e.g. as described on WO 2002/097406, the content of which is herein incorporated by reference, or a quantum well laser.

In a preferred embodiment, light is irradiated into the support, whereby an evanescent excitation field is generated by way of internal reflection at the support surface in the region of the molecules to be analysed. Internal reflection at one or more positions of the support surface in the region of the molecules to be analysed, generates an evanescent excitation field which causes excitation of labelling groups present in the respective spots. In an especially preferred embodiment, the detection involves a total internal reflection (TIR), particularly total internal reflection fluorescence (TIRF) detection.

Diffractive optical elements (DOEs) may be used to provide multi-point illumination on the support. DOEs may also be used in detection methods involving internal reflection, e.g. by introducing a diffractive optical element into the exciting light beam in a TIR(F) setup.

According to the present invention, light emitted from the single molecules is detected with a light detector which comprises a plurality of detection pixels aligned with a matrix of sample spots on the support. Preferably, the detector is a multipoint single photon avalanche detector (SPAD). It combines high sensitivity over a broad spectral range, e.g. 350-900 nm with a high time resolution of e.g. ≤1 ns, which is advantageous when the lifetime of an excited fluorescent state is to be used for molecular analysis.

For an exact identification of a labelling group, e.g. a fluorescent labelling group, the lifetime of the excited state is preferably determined together with a wavelength-specific emission. The lifetime is preferably in the range between 1-6 ns. From a combination of parameters selected from lifetime, characteristic count rate per molecule (determined by wavelength-dependent laser intensity), excitation coefficient (e.g. about $10^5$/M cm), quantum yield (e.g. 0.3-0.9), and/or wavelength-dependent detector sensitivity, the identification of the labelling group can be carried out without application of specific wavelength-dependent emission filters.

Further, it is preferred to carry out a pulsed excitation of the single molecules to be analysed in order to eliminate or reduce straylight caused by Raleigh and Raman scattering as well as formation of triplet states and photon bleaching. A preferred pulse excitation time is less than 1 ns, e.g. about 50-500 ps.

The diameter of individual detection pixels on the detector is usually about 0.5 µm-50 µm. The individual detection pixels are separated by a distance (i.e. the pixel pitch length), the length of which is at least the pixel diameter, preferably at least about 2 times, more preferably at least about 3-10 times, the diameter of the detection pixel. Preferably, the distance between pixels on the detector is about 2-200 µm, more preferably about 4-150 µm.

As outlined above, an optical projection of the detection pixels is formed on the support. The optical projections on the supports are e.g. about 10-200 times or about 40-120 times smaller than the size of the detection pixels on the detector. The optical projections on the supports should correspond to the distances between the centres of individual sample spots on the support. Hence, the optical projections usually have a diameter of about 20 nm to about 1 µm, preferably about 100-600 nm.

The distance between the centers of individual detection pixel projections on the support (i.e. the projection pitch length) is preferably at least about 2 times the size of the centers of individual detection pixel projections on the support, more preferably at least about 3 times, at least about 5 times, at least about 10 times. The upper limit may be up to about 5000 nm, such as up to about 1000 nm, up to about 500 nm, up to about 100, or up to about 50 times the size of the spot diameter. The distance between the centers of individual detection pixel projections on the support may have a distance range which is selected from any value of the lower and upper limits, e.g. from about 2 up to about 5000 times, or about 2 up to about 500 times, e.g. about 2 up to about 100 times about 5 to 500 times the distance of centers of individual detection pixel projections on the support.

In a preferred embodiment, the process of the invention is used for the sequencing of single nucleic acid molecules. In this embodiment, the process preferably comprises the steps:
providing at an individual sample spot of the support (i) a single nucleic acid molecule, (ii) a nucleic acid-synthesizing enzyme molecule and/or a nucleic acid degrading enzyme molecule, and (iii) fluorescence labelled nucleotide building blocks in free form and/or incorporated into the nucleic acid molecule,
conducting an enzymatic reaction, wherein nucleotide building blocks are incorporated into and/or cleaved off from said single nucleic acid molecule, and
individually determining the base sequence of the nucleic acid molecule on the basis of the time-dependent fluorescence change, caused when nucleotide building blocks are incorporated into and/or cleaved off from said single nucleic acid molecule.

Both incorporation of nucleotide building blocks into a nucleic acid molecule and cleaving off nucleotide building blocks from a nucleic acid molecule may cause a time-dependent change in the fluorescence emission of labelling groups.

In embodiments involving sequencing by degradation, a nucleic acid-degrading enzyme molecule is contacted with a nucleic acid molecule to be sequenced having incorporated labelling groups, particularly fluorescence labelling groups.

In embodiments involving sequencing by elongation, a nucleic acid-synthesizing enzyme molecule is contacted with a nucleic acid molecule to be sequenced having annealed thereto a primer and free nucleotide building blocks with labelling groups, particularly fluorescence labelling groups.

In one embodiments involving sequencing by elongation, a nucleic acid synthesizing enzyme molecule is contacted with a nucleic acid molecule to be sequenced having annealed Therese a primer and free nucleotide Building blocks with labelling groups, particularly fluorescent labelling groups. Sequencing by elongation may also comprise nucleic acid amplification, i.e. the synthesis of a plurality of nucleic acid molecules from a single template.

In one embodiment, a nucleic acid synthesising enzyme molecule and/or and/or a nucleic acid degrading enzyme molecule may be immobilized, e.g. on the support, or on a nanoparticle positioned on the support. The nucleic acid molecule to be sequenced is present in free form and thus may be concentrated at the sample spot by applying the electrical field as described above.

In one embodiment, the present application relates to a process for sequencing an individual nucleic acid molecule, comprising the following steps:
(a) providing at least one nucleic acid-synthesizing enzyme molecule in immobilized form,
a circular or linear nucleic acid template in free form, a primer annealed to said template or capable of annealing to said nucleic acid template, and fluorescence-labelled nucleotide building blocks,
(b) generating a nucleic acid molecule complementary to the sequence of the nucleic acid template molecule having incorporated said nucleotide building blocks in a primer elongation catalyzed by said immobilized nucleic acid-synthesizing enzyme molecule,
(c) optionally contacting said generated nucleic acid molecule with a nucleic acid-degrading enzyme molecule and cleaving off individual nucleotide building blocks from said generated nucleic acid molecule in a nuclease digestion catalyzed by said nucleic acid-degrading enzyme molecule, and
(d) determining the base sequence of said nucleic acid template molecule on the basis of the time-dependent fluorescence change, caused when nucleotide building blocks are incorporated during primer elongation and/or cleaved off during nuclease digestion.

In a further embodiment, the present application relates to a process, comprising the following steps:
(a) providing at least one nucleic acid-degrading enzyme molecule in immobilized form, and a nucleic acid molecule comprising fluorescence-labelled nucleotide building blocks in free form,
(b) contacting said nucleic acid-degrading enzyme molecule with said nucleic acid molecule, and cleaving off individual nucleotide building blocks from said nucleic acid molecule in a nuclease digestion, catalyzed by said nucleic acid-degrading enzyme molecule, and
(c) determining the base sequence of said nucleic acid molecule on the basis of the time-dependent fluorescence change, caused when nucleotide building blocks are cleaved off during nuclease digestion.

The process of the invention is a support-based multiplex sequencing method which enables a multiplicity of individual nucleic acid molecules to be sequenced. This is achieved by providing a reaction space comprising a nucleic acid molecule to be sequenced, and a nucleic acid-degrading and/or nucleic acid-synthesizing enzyme for determining in parallel time-dependent fluorescence change in a plurality of nucleic acid synthesis and/or degradation reactions. The process is preferably carried out in the form of a parallel high throughput single molecule analysis.

In a preferred embodiment, a nucleic acid-synthesizing enzyme molecule is provided in immobilized form. A nucleic acid-degrading enzyme molecule may also be present in immobilized form or in free form. In still other embodiments, hybrids and/or conjugates of nucleic acid-synthesizing enzyme molecules and nucleic acid-degrading enzyme molecules, e.g. genetic fusions and/or conjugates linked by bi-functional linker molecules, may be used.

The enzyme molecules may be immobilized via covalent or noncovalent interactions. For example, high-affinity interactions between the partners of a specific binding pair, for example biotin/streptavidin or avidin, hapten/anti-hapten antibody, sugar/lectin, etc., can mediate immobilizing of the polypeptides or nucleic acids. Thus it is possible to couple biotinylated enzyme molecules to streptavidin-coated surfaces. Alternatively, the enzyme molecules may also be immobilized via adsorption. Thus enzyme molecules modified by incorporation of alkane thiol groups, may bind to metallic supports, e.g. supports made of gold. Yet another alternative is covalent immobilization in which it is possible to mediate enzyme or nucleic acid molecule binding via reactive silane groups on a silica surface.

According to the invention, at least one single molecule is analysed. Preferably a plurality of single molecules is analysed. These molecules are located at the sample spots on the support. They are in contact with a sample liquid, which contains the free reaction partners. Thereby, one or more reaction spaces are defined. Preferably at least 100, particularly preferably at least 1000, and particularly preferably at least 10 000, and up to more than $10^6$, molecules may be analysed on a single support, e.g. a single planar support.

The molecules to be immobilised on the sample spots, e.g. enzyme molecules may be applied to specific spots on the support surface, for example by contacting a diluted solution of biotinylated molecules with a support, only particular regions of which are coated with streptavidin. In embodiments where the nucleic acid-degrading enzyme molecules are immobilized, they may be co-immobilized with nucleic acid-synthesizing enzyme molecules, i.e. both types of enzyme molecules are bound in the same spots of the support surface.

The nucleic acid molecule whose sequence is to be determined may be selected, for example, from DNA molecules such as genomic DNA fragments, cDNA molecules, plasmids, etc., or else from RNA molecules such as mRNA molecules. The nucleic acid molecule may originate from genomic or expression libraries, generated from cells or organisms, e.g. eukaryotic or prokaryotic cells or organisms. The process of the present invention allows parallel sequencing of a plurality of identical, equal or different nucleic acid template molecules, e.g. at least 10, 100, 1.000 or 10.000 and up to 100.000, $10^6$ or $10^7$ or even more identical, equal or different nucleic acid molecules.

Preferably, the nucleic acid molecules to be sequenced are single-stranded nucleic acid molecules in a linear or circular form, e.g. in a covalently linked circular form. In order to obtain a circular nucleic acid template, a linear nucleic acid molecule may be subjected to a circularization procedure and optionally a strand-separation procedure during sample preparation. Circularization may be effected by ligation according to known protocols, e.g. using DNA or RNA ligases. In some embodiments, an adaptor and/or identifier molecule, i.e. a nucleic acid molecule of known sequence, may be coupled to the nucleic acid molecule.

The nucleic acid molecules are preferably from 20 to 5000000 nucleotides, particularly preferably from 50 to 1000000 or from 100 to 100000 nucleotides, in length. The process is specifically suited for sequencing nucleic acid molecules with above 150 nucleotides, above 500 nucleotides, above 1000, above 10000, above 500000. The sequence determination may comprise nucleic acid elongation and/or nucleic acid degradation. The sequencing process includes one or more sequencing cycles.

The nucleic acid-synthesizing enzyme molecules are capable of elongating a primer annealed to a nucleic acid template molecule. Preferably, primer elongation is carried out by progressively incorporating individual nucleotide building blocks at the 3'-terminus of a growing nucleic acid chain, wherein a nucleic acid molecule complementary to the sequence of the circular nucleic acid template is generated. The nucleic acid-synthesizing enzymes are selected from polymerases capable of a template specific nucleic acid polymerization, preferably from DNA polymerases and RNA polymerases, e.g. natural or modified polymerases, including thermostable DNA polymerases.

Specific examples of suitable DNA polymerases include Taq polymerases, exonuclease-deficient Taq polymerases, E. coli DNA polymerase I, Klenow fragment, reverse transcriptase, φ29-related polymerases including wild-type φ29 polymerase and derivatives of such polymerases, such as exonuclease-deficient forms, T7 DNA polymerase, T5 DNA polymerase, an RB69 polymerase and others.

The nucleic acid-degrading enzyme molecules are capable of progressively cleaving off individual nucleotide building blocks from a nucleic acid molecule. Preferably exonucleases, more preferably single-strand exonucleases which degrade in the 3'→5' direction or in the 5'→3' direction are used. Exonucleases which are particularly preferably used are 3'→5' exonucleases such as E. coli exonuclease I and E. coli exonuclease III, and 5'→3' exonucleases such as T7 exonuclease, E. coli exonuclease II and E. coli exonuclease VIII. Further, the exonuclease activities of various polymerases, e.g. the Klenow fragment, Taq polymerase or T4 polymerase may be used.

The nucleic acid-synthesizing enzyme molecules are contacted with a linear or circular nucleic acid template molecule, e.g. a single-stranded DNA or RNA molecule, and a primer molecule annealed to the nucleic acid template molecule or capable of annealing thereto. The primer molecule is preferably a single-stranded nucleic acid or nucleic acid analogue molecule having a free 3'-end which can be extended by an enzymatic reaction catalyzed by the immobilized nucleic acid-synthesizing enzyme molecules. The length of the primer molecule is selected to allow effective annealing to the template under reaction conditions. Usually, the length of the primer molecule is at least 8, at least 10, at least 12 or at least 15 nucleotides and e.g. up to 20, 25, 50 or 100 nucleotides, or even higher. In some embodiments, the primer is resistant against digestion by nucleic acid-degrading enzyme molecules, e.g. by incorporating nucleotide analogue building blocks and/or linkages between nucleotide building blocks, which are stable against degradation. In other embodiments, the primer is sensitive against digestion by nucleic acid-degrading enzyme molecules.

The sequence of the primer is selected in that it effectively anneals under reaction conditions to the template molecule. For instance, the primer may be a universal degenerated primer capable of statistically annealing to unknown nucleic acid sequences. In other embodiments, the primer may be capable of annealing to a known sequence portion of the nucleic acid template molecule. In this embodiment, a known adaptor and/or identifier sequence may be incorporated into the nucleic acid template molecule. The primer may be unlabelled or comprise fluorescent labelling groups.

Further, the presence of nucleotide building blocks carrying at least one fluorescent labelling group is required, Preferably, each different nucleotide building block (A, G, C, T/U) contains a different fluorescent labelling group.

The fluorescent labelling groups may be selected from known fluorescent labelling groups used for labelling biopolymers, particularly nucleic acids, such as, for example, fluoresceins, rhodamines, oxazines, for example Evoblue or Gnothis Blue, phycoerythrin, Cy3, Cy5, IR dyes or derivatives thereof, etc.

The nucleotide building blocks may carry (i) a fluorescence labelling group which remains with the building block when the building block is incorporated into a nucleic acid molecule during a primer elongation catalyzed by a nucleic acid-synthesizing enzyme molecule, and/or (ii) a fluorescence labelling group which is cleaved off from the building block when the building block is incorporated into a nucleic acid molecule during a primer elongation catalyzed by a nucleic acid-synthesizing enzyme molecule. Fluorescence labelling groups remaining with the building block are preferably attached to the α-phosphate group, to the sugar and/or to the nucleobase group. Preferably, fluorescence labelling groups remaining with the building block are attached to the nucleobase, e.g. via a linker which may have a chain-length of up to 15, preferably of 10-12 carbon atoms, optionally including heteroatoms, e.g. N, O or S atoms. Fluorescence labelling groups which are cleaved off when the building block is incorporated into a nucleic acid molecule may be attached to a terminal phosphate group, e.g. of a hexa-, penta-, tetra- or triphosphate building block such as the y-phosphate group of a triphosphate building block. In certain embodiments, building blocks are selected which contain both (i) a fluorescence labelling group remaining after incorporation and (ii) a fluorescence labelling group cleaved off during incorporation. In this case, fluorescence groups capable of interacting with each other, e.g. by quenching and/or energy transfer, may be selected.

The nucleic acid molecules to be sequenced will contain fluorescent labelling groups in case the nucleic acid molecule is subjected to direct sequencing using a nucleic acid-degrading enzyme molecule. On the other hand, the nucleic acid molecule to be sequenced may not contain fluorescent labelling groups, if the nucleic acid molecule is used as a template in a primer elongation.

The process of the present invention may involve a step of generating nucleic acid molecules having incorporated nucleotide building blocks in a primer elongation catalyzed by the nucleic acid-synthesizing enzyme molecules and/or a second step of cleaving off individual nucleotide building blocks from the generated nucleic acid molecules catalyzed by nucleic acid-degrading enzyme molecules. Dependent on the type of fluorescence labels, nucleic acid sequence determination may be carried out during primer elongation and/or during degradation.

Sequence determination during the primer elongation involves the use of nucleotide building blocks carrying a fluorescence-labelling group which is cleaved off from the building block when it is incorporated into a nucleic acid molecule. In this case, a time-dependent fluorescence change caused by cleaving off the fluorescence-labelling group from the nucleotide building block may be determined. Sequence determination during nucleic acid degradation involves the use of a nucleotide building block, which carries a fluorescence-labelling group which remains with the building block when it is incorporated into a nucleic acid molecule. Progressive cleavage of individual nucleotide building blocks from the nucleic acid molecules causes a time-dependent change of fluorescence when the labelled nucleotide building block is liberated from the nucleic acid molecule. In certain embodiments, it is also possible to carry out a sequence determination during elongation and degradation, i.e. when using nucleotide building blocks, which both carry a fluorescence-labelling group remaining with the building block and a fluorescence-labelling group which is cleaved off from the building block when the building block is incorporated into a nucleic acid molecule. In this embodiment, both fluorescent groups may be the same or different.

In some embodiments, the method of the invention involves one or more cycles of nucleic acid-synthesis and nucleic acid-degradation in order to determine the base sequence of a nucleic acid molecule template. The nucleic acid synthesis involves an elongation of the primer annealed to the nucleic acid template molecule catalyzed by the nucleic acid-synthesizing enzyme molecule, wherein a nucleic acid molecule complementary to the sequence of the nucleic acid template is generated. In the next step, the generated nucleic acid molecule is degraded by a nucleic acid-degrading enzyme molecule.

When a nucleotide building block is incorporated into an elongated nucleic acid molecule, a time dependent change in the fluorescence may occur, which can be detected as indicated above. Preferably, the incorporation of the nucleotide building blocks into the elongated nucleic acid molecule is associated with a detectable increase in the fluorescence, preferably with a transient increase in the fluorescence. For example, nucleotide building blocks may be used which carry a fluorescent labelling group on the portion of the molecule which is cleaved off when the building block is incorporated into the primer, e.g. on the y-phosphate group.

When a nucleotide building block is cleaved off from the synthesized nucleic acid molecule, a time-dependent change of fluorescence may be determined due to the interaction of fluorescent labelling groups incorporated in nucleic acid strands with neighbouring groups, for example with chemical groups of the nucleic acids, in particular nucleobases such as, for example, G, or/and neighbouring fluorescent labelling groups, and these interactions leading to a change in fluorescence, in particular in fluorescence intensity, compared to the fluorescent labelling groups in "isolated" form, owing to quenching processes or/and energy transfer processes. The removal by cleavage of individual nucleotide building blocks alters the overall fluorescence, for example the fluorescence intensity of an immobilized nucleic acid strand, and this change is a function of the removal by cleavage of individual nucleotide building blocks, i.e. a function of time.

This time-dependent change in fluorescence during elongation and/or degradation may be recorded in parallel for a multiplicity of nucleic acid molecules and correlated with the base sequence of the individual nucleic acid strands. Preference is given to using those fluorescent labelling groups which, when incorporated in the nucleic acid strand, are, at least partially, quenched so that the fluorescence intensity is increased after the nucleotide building block containing the labelling group or a neighbouring building block causing quenching has been removed by cleavage.

During incorporation and/or removal of individual nucleotide building blocks, it is possible to measure a change in fluorescence intensity of the nucleic acid strand or/and the incorporated or cleaved-off nucleotide building block, owing to quenching processes or energy transfer processes. This change in fluorescence intensity with time depends on the base sequence of the nucleic acid strand studied and can therefore be correlated with the sequence.

The complete sequence of the nucleic acid molecule may be determined by using a mixture of nucleotide building blocks, labelled on all four different bases, for example on A, G, C and T, or on combinations of two or three different bases. It is possible, where appropriate, to attach to the nucleic acid strand to be studied also a "sequence identifier", i.e. a labelled nucleic acid of known sequence, for example by enzymatic reaction using ligase or/and terminal transferase, so that at the start of sequencing initially a known fluorescence pattern and only thereafter the fluorescence pattern corresponding to the unknown sequence to be studied is obtained.

The detection comprises irradiating light into the support, preferably by means of a laser, or by another suitable light source, in order to cause excitation of the fluorescent labelling groups. It is possible, in this connection, to use one or more laser beams, for example an expanded laser beam, having a cross section of approx. 1-20 mm, or/and multiple laser beams. The detection preferably comprises a multi-point fluorescence excitation by lasers, for example a dot matrix of laser dots generated via diffraction optics (cf. WO 2002/097406) or a quantum well laser.

Fluorescence emission of a plurality of nucleic acid strands may be detected in parallel using a detector matrix which comprises, for example, an electronic detector matrix, for example a CCD camera, a CMOS detector matrix, e.g. a CMOS camera, or an avalanche photodiode matrix. The detection may be carried out in such a way that fluorescence excitation and detection are carried out in parallel on all nucleic acid strands studied. A possible alternative to this is to study in several steps in each case a portion of the nucleic acid strands. Preference is given to carrying out the detection on fluorescence light which is emitted essentially orthogonally from the support surface through the reaction space or through the support body.

The detection may be carried out, for example, by fluorescence correlation spectroscopy which involves exposing a very small volume element for example from $10^{-10}$ to $10^{-24}$ l, to the excitation light of a laser, or another suitable light source, which light excites the receptors present in this measuring volume so that the latter emit fluorescence light, the fluorescence light emitted from said measuring volume being measured by means of a photodetector and the change in the measured emission with time being correlated with the concentration of the analyte, so that it is possible to identify, at an appropriately high dilution, individual molecules in said measuring volume. The small volume element can be provided by means of using optics providing a confocal volume element or by means of a volume element established by total internal reflection (TIR). Details of the procedure and of the apparatus used for detection can be found in the disclosure of the European patent 0 679 251. The confocal determination of single molecules is furthermore described in Rigler and Mets (Soc. Photo-Opt. Instrum. Eng. 1921 (1993), 239 ff.) and Mets and Rigler (J. Fluoresce 4 (1994) 259-264).

Alternatively or additionally, detection may also be carried out by way of time-resolved decay measurement, called "time gating", as described, for example, by Rigler et al., "Picosecond Single Photon Fluorescence Spectroscopy of Nucleic Acids", in: "Ultrafast Phenomenes", D. H. Auston, Ed., Springer 1984. Here, the fluorescent molecules are excited in a measuring volume followed by, preferably at a time interval of ≥100 ps, opening a detection interval on the photodetector. In this way it is possible to keep background signals generated by Raman effects sufficiently low so as to enable single molecules to be detected in an essentially interference-free manner.

The invention also relates to an apparatus for analysing at least one individual single molecule, e.g. for sequencing at least one single nucleic acid molecule, comprising:
(i) a support comprising at least one individual sample spot thereon, wherein said sample spot is at least partially made from an electrically conductive material,
(ii) means adapted for contacting said support with a liquid medium comprising at least one single molecule to be analysed,
(iii) means adapted for applying an electrical field across a reaction space which is formed upon contacting the support with liquid medium,
(iv) a light source which provides at least one individual illuminated volume element at a sample spot on the support, for individually illuminating a single molecule at an individual sample spot, and
(v) a light detector for individually detecting light emitted from a single molecule at an individual sample spot.

The invention further relates to an apparatus for analysing a plurality of individual single molecules or a plurality of individual single nucleic acid molecules in parallel, comprising:
(i) a support comprising a plurality of individual sample spots thereon, wherein said sample spots are at least partially made from an electrically conductive material, means adapted for contacting said support with a liquid medium comprising a plurality of single molecules to be analysed,
(iii) means adapted for applying an electrical field across a reaction space which is formed upon contacting the support with liquid medium,
(iv) a light source which provides at least one individual illuminated volume element at a sample spot on the support, for individually illuminating a single molecule at an individual sample spot, and
(v) a light detector for individually detecting light emitted from a plurality of single molecules at individual sample spots in parallel.

The electrically conductive spots on the support surface may be made from e.g. areas of metal or semi-metal. Metal spots may be prepared by vapour deposition of metals such as Au, Ag, Al, Cr, Ni and others, which are vapourized on a support covered by a grid mask, which may be produced by electrobeam lithography or equivalent technologies. The size of holes in the grid mask may correspond to the size of the spots on the support surface. Preferably, the hole diameter in the grid mask is 5 nm or less. Alternatively, the spots on the support may be prepared by site-specific deposition of electrically conductive nanoparticles, e.g. having a size of 2-10 nm, by zeptoliter precision pipetting of particles on the support, particularly on a support having a planar surface. The particles may have a surface selected from metal such as Au, Ag, Al, Cr, Ni or others, or semi-metal. The spot surface areas on the support and/or the particles may be modified by biotin and/or streptavidin or other affinity reagents as described above.

The sample spots on the support are preferably aligned to the center of the projection of individual detection pixels. Adjustment of the alignment between sample spots and detection pixel projections may be carried out by a nanometer precision piezo-adjustment element in a detector-driven feedback loop. The adjustment tolerance between the center of a sample spot and the center of a detection pixel projection is preferably about 5 nm or less, about 2 nm or less or about 1 nm or less The process of the invention and the apparatus of the invention may be employed, for example, in the analysis of genomes and transcriptomes or in differential analyses, for example studies regarding the difference in the genome or transcriptome of individual species or organisms within a species. Particularly preferred is the determination of the frequency and/or distribution of individual subsequences within a population of sequences, e.g. of at least 10, at least $10^2$, at least $10^3$ or at least $10^4$ individual sequences.

In a preferred embodiment, the process of the invention and the apparatus of the invention may be employed in the analysis of quasi-species sequences (cf. M. Eigen et al., "Molecular Quasi Species", *J. Phys. Chem.* 92, December 1988, 6881-6891; M. Eigen & C. Biebricher, "Role of Genome Variation in Virus Evolution", in *RNA Genetics*, Vol. 3: Variability of RNA Genomes; CRC Press 1988; M. Eigen & R. Winkler-Oswatitsch, "Statistical Geometry on Sequence Space", in *Molecular Evolution: Computer Analysis of Protein and Nucleic Acid Sequences*, Academic Press, 1990, M. Eigen et al., "The Hypercycle-Coupling of RNA and Protein Biosynthesis in the Infection Cycle of an RNA Bacteriophage", *Biochemistry* 30, November 1991, 11005-11018, M. Eigen, "Viral Quasispecies", *Scientific American*, July 1993, 42-49, E. Domingo et al. "Quasispecies and RNA Virus Evolution: Principles and Consequences", *Landes Bioscience Madame Curie Database,* 2000 and references recited therein).

By means of single molecule sequencing, the distribution of individual sequences within a population of organisms within a species or within a population of cells within an organism may be determined. For example, populations of organisms, such as bacteria or viruses, or populations of cells, such as spermatozoa, do not contain identical genetic information in certain sequences of their genomes. Instead, there are distinct individual sequences (corresponding to so-called quasi-species or sub-species) present, which differ in one or several, e.g. 2, 3 or 4 nucleotides, over a given length. The present invention now allows exact determination of individual variant sequences by means of single molecule sequencing, particularly by means of repeated cycles of single molecule sequencing of individual variants. Thereby, the frequency and distribution of individual sub-sequences within a population of organisms, e.g. viral or bacterial organisms, or a population of cells, e.g. spermatozoa, may be determined. By means of this information, the distribution of sub-species within a given population of organisms or a population of cells may be exactly determined. This allows—in case of pathogenic organisms such as bacteria or viruses—an improved diagnosis and therapy, e.g. by detecting the presence or absence of drug-resistant mutations. In case of cells such as spermatozoa, an improved genetic analysis, e.g. by detecting the presence or absence of certain genotypes, may be carried out.

Furthermore, the figures below are intended to illustrate the present invention.

FIG. 1 shows a first embodiment of a device according to the present invention. An optically transparent support (10) comprises a plate of a non-conductive base material, e.g. glass or quartz (12). It is coated with an electrically conductive layer (14) e.g. of indium tin oxide. On the planar support surface, electrically conductive sample spots (16) are located. The sample spots comprise a base layer from a first metal, e.g. Cr (18), and a second (top) layer from a second metal, e.g. a noble metal such as Au (20). An electrical field is applied between the electrically conductive sample spots (16) and a second electrode (22), which may be a portion of the optical measuring device, e.g. the metal case and/or the tip of the optical objective.

A reaction space (24) is generated by contacting the support (10) with a liquid medium comprising single molecules, e.g. nucleic acid molecules (28) to be analysed. By applying the electrical field, the nucleic acid molecules are concentrated at, i.e. in the area of or around the sample spots (16). On the sample spots (16), nucleic acids degrading and/or synthesising enzyme molecules (26) are immobilised. Upon contact of the nucleic acid molecules (28) with the immobilised enzyme molecules (26), nucleic acid synthesis and/or degradation will occur leading to a time-dependent change in fluorescence emitted by fluorescent marker groups (not shown).

FIG. 2 shows a further embodiment of a device according to the present invention. Here, a support (30) comprising a plurality of microwells (32a, 32b) is provided. Preferably, the support is optically transparent. The microwells comprise electrically conductive sample spots (16) comprising metal layers (18) and (20), e.g. as described above. An electrical field is applied between the sample spots (16) and electrodes (34a, 34b) provided in the microwell walls. By applying an electrical field between the sample spots (16) and the electrodes (34a, 34b), single molecules (28) present in individual reaction spaces within wells (32a, 32b) are concentrated at the sample spots (16) where nucleic acid synthesising and/or degrading enzyme molecules (26) are immobilised.

The invention claimed is:

1. A process for analysing a single molecule (28) comprising the following steps:
   (a) providing a planar support (10) comprising a plurality of individual sample nano-spots (16) thereon, wherein said sample nano-spots (16) are at least partially made from an electrically conductive material,
   (b) contacting said support (10) with a liquid medium comprising at least one single molecule (28) to be analysed, whereby a reaction space (24) of liquid medium on said sample nano-spots (16) is formed,
   (c) applying an electrical field across said reaction space (24), wherein the electrical field is applied with a direct current voltage, whereby a concentration of said at least one single molecule (28) to be analysed at said sample nano-spots (16) is effected, and
   (d) individually analysing said at least one single molecule (28),
   wherein
   the single molecule at an individual sample nano-spot is illuminated by a light source providing an illuminated volume element, the volume element being an evanescent field generated by total internal reflection, wherein the reaction space is a single reaction space which is formed across the support on which the sample spots are located, wherein the reaction is carried out in said single reaction space, wherein an optical projection of a detection pixel on the support has a diameter in the range of about 100 nm-5 µm and wherein an individual sample nano-spot is aligned to the projection of a single detection pixel on the planar support.

2. The process of claim 1, wherein the at least one single molecule (28) is at least one nucleic acid molecule, and wherein step (d) comprises sequencing of the at least one single nucleic acid molecule.

3. The process of claim 2, wherein the at least one single molecule (28) is a plurality of nucleic acid molecules, and wherein step (d) comprises sequencing of the plurality of single nucleic acid molecules.

4. The process of claim 1, wherein said plurality of individual sample nano-spots have a diameter in the range of about 1-20 nm and the distance between each individual nano-spot (16) is at least about 2 times the diameter of the nano-spot (16).

5. The process of claim 4, wherein the distance between each individual nano-spot (16) is about 3-500 times the diameter of the nano-spot (16).

6. The process of claim 1, wherein the support (10) has a structured surface.

7. The process of claim 1, wherein the support (10) has an electrically conductive surface in the area between individual sample nano-spots (16).

8. The process of claim 1, wherein the surface of the sample nano-spot (16) is a metal selected from the group consisting of Au, Ag, Cr, Ni and Al.

9. The process of claim 8, wherein the metal is Au.

10. The process of claim 1, wherein the surface of the sample nano-spot (16) has bound thereto a nucleic acid-synthesizing enzyme and/or a nucleic acid-degrading enzyme.

11. The process of claim 1, wherein the electrical field has a field strength of about 1-5000 V/cm.

12. The process of claim 11, wherein the electrical field has a field strength of about 10-2000 V/cm.

13. The process of claim 12, wherein the electrical field has a field strength of about 20-200 V/cm.

14. The process of claim 1, wherein the electrical field is applied between the support surface and a further electrode (22, 34a, 34b), which may be an electrically conductive structure of an optical measuring device.

15. The process of claim 1, further comprising determining the frequency and/or distribution of subsequences with a population of sequences.

16. The process of claim 15, wherein the population comprises at least $10^2$ individual members.

17. The process of claim 16, wherein the population comprises at least $10^3$ individual members.

18. The process of claim 17, wherein the population comprises at least $10^4$ individual members.

19. A process for analysing a plurality of single molecules (28), comprising the following steps:
  (a) providing a planar support (10) comprising a plurality of individual sample nano-spots (16) thereon, wherein said sample nano-spots (16) are at least partially made from an electrically conductive material,
  (b) contacting said support (10) with a liquid medium comprising a plurality of single molecules (28) to be analysed, whereby one reaction space (24) on said sample nano-spots (16) is formed,
  (c) applying an electrical field across said reaction space (24), wherein the electrical field is applied with a direct current voltage, whereby a concentration of said single molecules (28) at said sample nano-spots (16) is effected, and
  (d) individually analysing said single molecules (28),
wherein
the plurality of single molecules at the individual sample nano-spots is illuminated by a light source providing illuminated volume elements, the volume elements being evanescent fields generated by total internal reflection, wherein the reaction space is a single reaction space which is formed across the support on which the individual sample nano-spots are located, wherein the reaction is carried out in said single reaction space, wherein an optical projection of a detection pixel on the support has a diameter in the range of about 100 nm-5 µm and wherein an individual sample nano-spot is aligned to the projection of a single detection pixel on the planar support.

* * * * *